US011557387B2

(12) United States Patent
Lee

(10) Patent No.: US 11,557,387 B2
(45) Date of Patent: Jan. 17, 2023

(54) ARTIFICIAL INTELLIGENCE ROBOT AND METHOD OF CONTROLLING THE SAME

(71) Applicant: LG ELECTRONICS INC., Seoul (KR)

(72) Inventor: Wonhee Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 427 days.

(21) Appl. No.: 16/490,336

(22) PCT Filed: May 2, 2019

(86) PCT No.: PCT/KR2019/005278
§ 371 (c)(1),
(2) Date: Aug. 30, 2019

(87) PCT Pub. No.: WO2020/222340
PCT Pub. Date: Nov. 5, 2020

(65) Prior Publication Data
US 2020/0411154 A1    Dec. 31, 2020

(51) Int. Cl.
*G08B 21/00* (2006.01)
*G16H 20/13* (2018.01)
(Continued)

(52) U.S. Cl.
CPC ............ *G16H 20/13* (2018.01); *A61J 7/0076* (2013.01); *G05D 1/0221* (2013.01);
(Continued)

(58) Field of Classification Search
CPC ........ G16H 20/13; G16H 40/67; G16H 40/63; G16H 50/20; A61J 7/0076; A61J 2200/30;
(Continued)

(56) References Cited

U.S. PATENT DOCUMENTS 9,361,021 B2    6/2016    Jordan et al.
2005/0154265 A1*  7/2005  Miro .................. G07C 9/37
                                              704/E15.045
(Continued)

FOREIGN PATENT DOCUMENTS

JP           5852706 B2       2/2016
JP        2018-175518 A       11/2018
(Continued)

*Primary Examiner* — Mark S Rushing
(74) *Attorney, Agent, or Firm* — Birch, Stewart, Kolasch & Birch, LLP

(57) ABSTRACT

An artificial intelligence (AI) robot includes a body for defining an exterior appearance and containing a medicine to be discharged according to a medication schedule, a support, an image capture unit for capturing an image within a traveling zone to create image information, and a controller for discharging the medicine to a user according to the medication schedule, reading image data of the user to determine whether the user has taken the medicine, and reading image data and biometric data of the user after the medicine-taking to determine whether there is abnormality in the user. The AI robot identifies a user and discharges a medicine matched with the user, so as to prevent errors. The AI robot detects a user's reaction after medicine-taking through a sensor, and performs deep learning, etc. to learn the user's reaction, to determine an emergency situation, etc. and cope with a result of the determination.

19 Claims, 11 Drawing Sheets

(51) Int. Cl.
*G16H 40/67* (2018.01)
*A61J 7/00* (2006.01)
*G05D 1/02* (2020.01)
*G06K 9/62* (2022.01)
*G06N 5/02* (2006.01)
*G08B 21/24* (2006.01)
*G06V 20/10* (2022.01)
*G06V 40/20* (2022.01)
*A61B 5/0205* (2006.01)
*A61B 5/024* (2006.01)

(52) U.S. Cl.
CPC .......... *G05D 1/0246* (2013.01); *G06K 9/6201* (2013.01); *G06N 5/02* (2013.01); *G06V 20/10* (2022.01); *G06V 40/20* (2022.01); *G08B 21/24* (2013.01); *G16H 40/67* (2018.01); *A61B 5/02055* (2013.01); *A61B 5/02438* (2013.01); *A61J 2200/30* (2013.01); *A61J 2200/70* (2013.01); *G05D 2201/0206* (2013.01)

(58) Field of Classification Search
CPC .... A61J 2200/70; A61J 7/0084; A61J 7/0418; A61J 7/0436; A61J 7/0454; A61J 7/0481; G05D 1/0221; G05D 1/0246; G05D 2201/0206; G05D 1/0094; G05D 1/0274; G05D 1/0282; G06K 9/6201; G06K 9/6271; G06N 5/02; G06N 3/0454; G06N 20/00; G06V 20/10; G06V 40/20; G06V 40/15; G06V 10/82; G06V 40/10; G06V 40/174; G08B 21/24; G08B 21/043; G08B 21/0476; A61B 5/02055; A61B 5/02438; A61B 5/0205; A61B 5/6887; A61B 5/7267; A61B 5/746; B25J 9/1679; B25J 9/0009; B25J 9/161; B25J 9/1664; B25J 9/1697; B25J 11/009; B25J 19/061
USPC .......................................................... 701/27
See application file for complete search history.

(56) References Cited

U.S. PATENT DOCUMENTS

2007/0198128 A1* 8/2007 Ziegler ................. G06N 3/008
                                                    700/245
2017/0105621 A1* 4/2017 Pratt ..................... G16H 50/20
2017/0266813 A1   9/2017 Davey et al.

FOREIGN PATENT DOCUMENTS

KR  10-2012-0075595 A   7/2012
KR  10-2014-0114218 A   9/2014
KR  10-2017-0127591 A   11/2017
KR  10-2018-0099434 A   9/2018

* cited by examiner

ARTIFICIAL INTELLIGENCE ROBOT AND METHOD OF CONTROLLING THE SAME

CROSS REFERENCE TO RELATED APPLICATIONS

This application is the National Phase of PCT International Application No. PCT/KR2019/005278, filed on May 2, 2019, which is hereby expressly incorporated by reference into the present application.

TECHNICAL FIELD

The present invention relates to an artificial intelligence robot which provides a medication service to a user, and more particularly to an artificial intelligence robot which measures biometric information of a user and provides the associated service to the user, and a method of controlling the same.

BACKGROUND ART

Robots have been developed for industry to take charge of a part of factory automation. Recently, robots have been applied to a wider variety of fields, like medical robots, aerospace robots, and home robots useable in homes. Among such robots, one that is movable by itself is referred to as an artificial intelligence (AI) robot.

With an increase in use of robots, there is increasing demand for robots capable of providing various information, entertainment and services over repetitive execution of simple functions.

Accordingly, a variety of robots have been developed which are disposed in homes, restaurants, shops, public places, etc. to provide convenience to persons.

In addition, services which remotely control robots to take care of patients have been proposed. For example, the cited reference (U.S. Pat. No. 9,361,021) performs a function of remotely controlling a robot to take care of a patient, and provides additional functions including selective display of information of the patient through a display, and display of a real-time image of the patient through the display.

The cited reference (Japanese registered patent No. JP5852706B9) remotely controls a robot to approach a user and provide various services to the user, and includes a variety of sensor cameras and a display in a system.

However, these remote control robots fail to personally approach users to provide the users with corresponding medicines to be taken thereby and confirm feedback from the users.

In robot services providing healthcare of users as mentioned above, it is just disclosed that an operator remotely controls a robot personally, and a spontaneous AI robot which identifies a person and discharges a corresponding medicine is not disclosed.

CITED REFERENCE

Patent Document

U.S. Pat. No. 9,361,021, Publication Date: Mar. 19, 2015

DISCLOSURE

Technical Problem

It is a first object of the present invention to provide an artificial intelligence robot which provides a medication service to a user and is a healthcare robot capable of identifying the user and discharging a medicine matched with the user, so as to prevent errors in medication time, medicine type, dose, etc.

It is a second object of the present invention to provide a healthcare robot which is capable of accurately recording a medication time of a user for utilization in future treatment and prescription.

It is a third object of the present invention to provide a healthcare robot which is capable of detecting, by a sensor, a user's reaction after medicine-taking upon medicine discharge, which is an event provided by the robot, and performing deep learning, etc. to learn the user's reaction, so as to determine an emergency situation, etc.

It is a fourth object of the present invention to provide a healthcare robot which is capable of, in response to a command about medication of a user received from a server or according to a predetermined schedule, identifying the user, discharging a specific medicine, capturing an image of a medicine-taking fact, and performing medicine-taking confirmation.

Technical Solution

In accordance with an aspect of the present invention, the above and other objects can be accomplished by the provision of a method of controlling an artificial intelligence (AI) robot, including matching, by the AI robot, a user with a medication target according to a medication schedule, discharging a medicine set for the user, reading image data of the user to determine whether the user has taken the medicine, reading image data of the user after the medicine-taking and reading a sense signal about biometric data of the user after the medicine-taking to determine whether there is abnormality in the user, and, when there is the abnormality in the user, generating an alarm and performing an emergency measure.

The AI robot may include a body including a medicine container formed inside thereof, the medicine container having a space defined to contain the medicine, and an inlet/outlet port formed on an outer surface thereof, the inlet/outlet port injecting or discharging the medicine therethrough.

The determining whether the user has taken the medicine may include acquiring image data of a medicine-taking action of the user after discharging the medicine, and comparing the acquired image data with image data of the medicine-taking action of the user in a previous cycle through deep learning to determine whether the user has taken the medicine.

The determining whether there is abnormality in the user may include acquiring the image data of the user after the medicine-taking, analyzing an action pattern of the user based on the acquired image data through the deep learning, acquiring the sense signal about the biometric data of the user after the medicine-taking, and combining the sense signal and the action pattern of the user to determine whether there is the abnormality in the user.

The biometric data may include information about a heart rate and a temperature of the user.

The matching a user with a medication target may include searching for the user while the AI robot moves, and matching image data of the searched user with information about the medication target upon acquiring the image data of the searched user.

The method may further include estimating a location where the user is existable and moving to the estimated location.

The AI robot may receive medication command information from a server according to the medication schedule.

The AI robot may receive information about the medication schedule directly from the user and search for the medication target according to the medication schedule stored therein.

The matching a user with a medication target may include calling a surrounding user through notification thereto according to the medication schedule and reading image data of the surrounding user to determine whether the surrounding user is the medication target.

In accordance with another aspect of the present invention, there is provided an artificial intelligence (AI) robot including a body for defining an exterior appearance of the AI robot and containing a medicine to be discharged according to a medication schedule, a support for supporting the body, an image capture unit for capturing an image within a traveling zone to create image information, and a controller for discharging the medicine to a user according to the medication schedule, reading image data of the user to determine whether the user has taken the medicine, and reading image data and biometric data of the user after the medicine-taking to determine whether there is abnormality in the user.

The controller, when there is the abnormality in the user, may perform a control operation to generate an alarm and perform an emergency measure.

The AI robot may further include an inlet/outlet port formed on an outer surface of the body to inject or discharge the medicine therethrough.

The controller may acquire image data of a medicine-taking action of the user after discharging the medicine, and compare the acquired image data with image data of the medicine-taking action of the user in a previous cycle through deep learning to determine whether the user has taken the medicine.

The controller may acquire the image data of the user after the medicine-taking, analyze an action pattern of the user based on the acquired image data through the deep learning, acquire the biometric data of the user after the medicine-taking, and combine the biometric data and the action pattern of the user to determine whether there is the abnormality in the user.

The biometric data may include information about a heart rate and a temperature of the user.

The support may include a traveling unit for moving the AI robot, wherein the controller may drive the traveling unit such that the AI robot searches for the user while moving.

The controller may estimate a location where the user is existable and drive the traveling unit to the estimated location.

The AI robot may receive medication command information from a server according to the medication schedule.

The AI robot may further include an interface for receiving information about the medication schedule directly from the user, wherein the storage unit may search for a medication target according to the medication schedule stored therein.

The AI robot may call a surrounding user through notification thereto according to the medication schedule and read image data of the surrounding user to determine whether the surrounding user is a medication target.

Advantageous Effects

Through the above technical solution, the present invention may identify a user and discharge a medicine matched with the user, so as to prevent errors in medication time, medicine type, dose, etc., thereby securing stability.

In addition, the present invention may accurately record a medication time of a user and whether the user has taken a medicine, for utilization in future treatment and prescription.

The present invention may detect, by a sensor, a user's reaction after medicine-taking on medicine discharge, which is an event provided by a robot, and perform deep learning, etc. to learn the user's reaction, so as to determine an emergency situation, etc. and cope with a result of the determination.

Further, the present invention may, in response to a command about medication of a user received from a server or according to a predetermined schedule, identify the user, discharge a specific medicine, capture an image of a medicine-taking fact, and perform medicine-taking confirmation, thereby enabling more reliable healthcare.

BEST MODE

Figure 1:
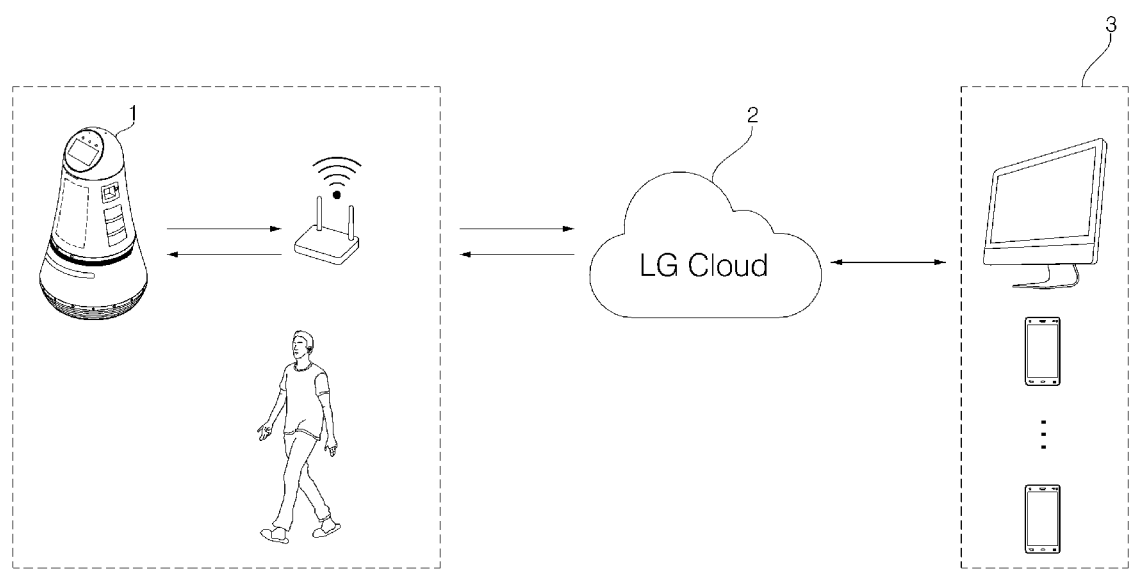
FIG. 1 is a view showing the configuration of an artificial intelligence (AI) robot system according to one embodiment of the present invention.

Expressions referring to directions such as "front (F)/rear (R)/left (Le)/right (Ri)/upper (U)/lower (D)" mentioned below are defined based on the illustrations in the drawings, but this is merely given to describe the present invention for clear understanding thereof, and it goes without saying that the respective directions may be defined differently depending on where the reference is placed.

The use of terms in front of which adjectives such as "first" and "second" are used in the description of constituent elements mentioned below is intended only to avoid confusion of the constituent elements, and is unrelated to the order, importance, or relationship between the constituent elements. For example, an embodiment including only a second component but lacking a first component is also feasible.

The thickness or size of each constituent element shown in the drawings may be exaggerated, omitted or schematically drawn for the convenience and clarity of explanation.

The size or area of each constituent element may not utterly reflect the actual size or area thereof.

Angles or directions used to describe the structure of the present invention are based on those shown in the drawings. Unless a reference point with respect to an angle or positional relationship in the structure of the present invention is clearly described in the specification, the related drawings may be referenced.

A medication service robot among artificial intelligence (AI) robots will hereinafter be described as an example with reference to FIGS. 1 to 3, but is not limited thereto.

Figure 2:
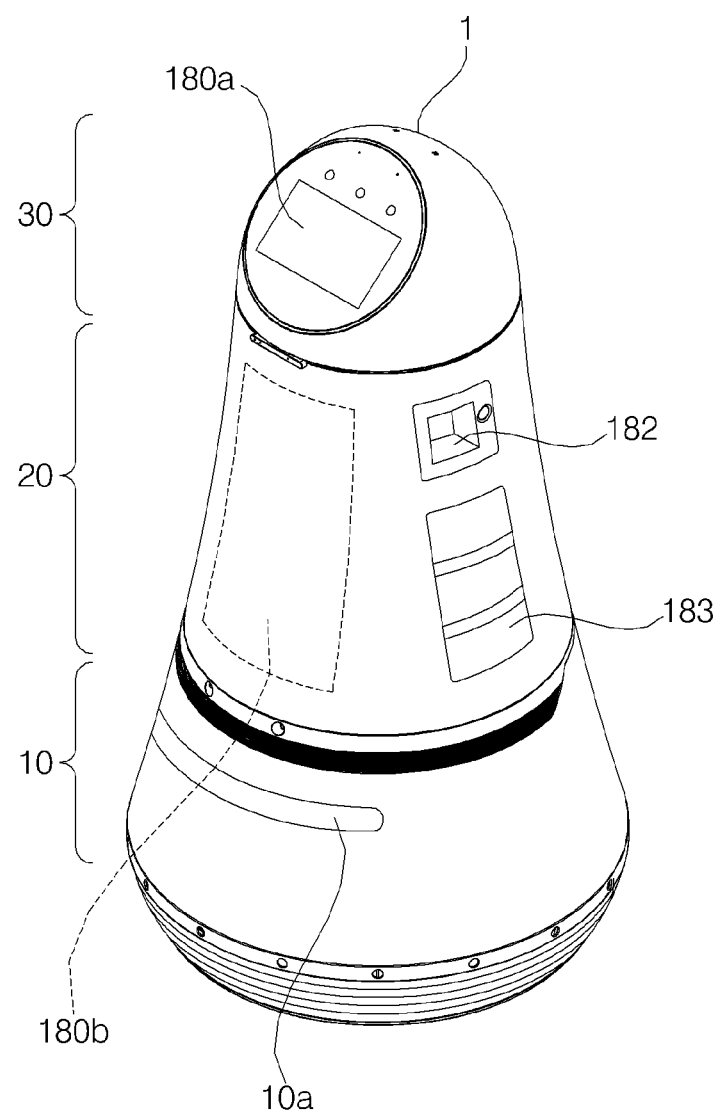
FIG. 2 is an elevation view of an AI robot in FIG. 1.
Figure 3:
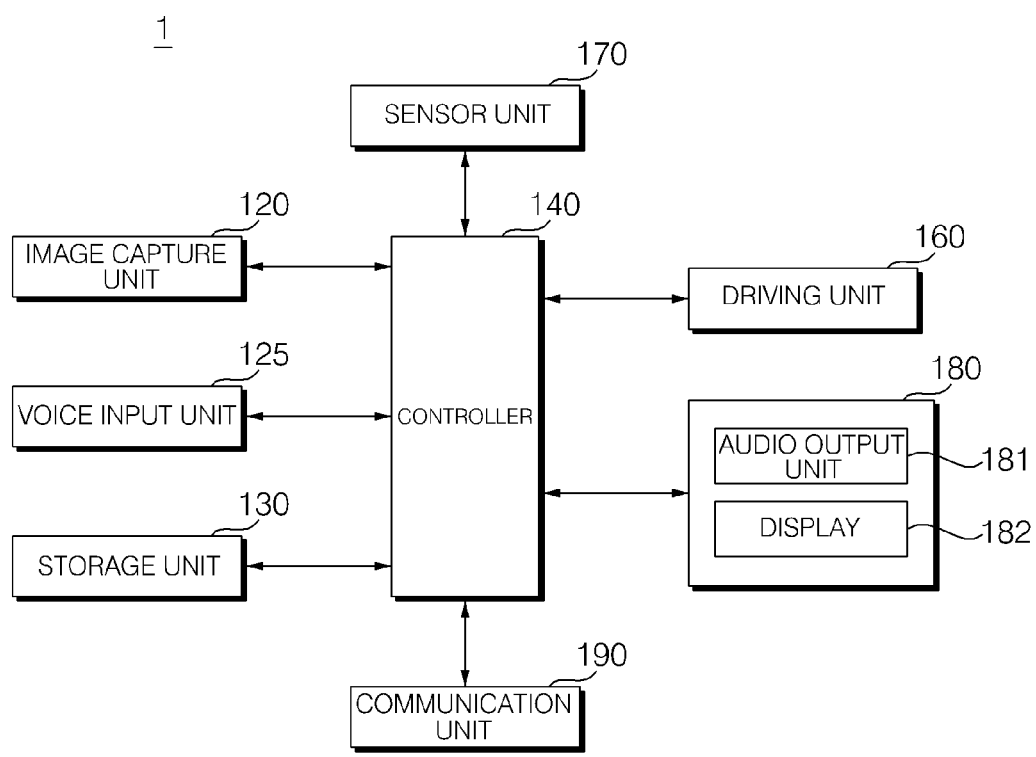
FIG. 3 is a block diagram illustrating a control relationship of the AI robot in FIG. 1.

FIG. 1 is a view showing the configuration of an AI robot system according to one embodiment of the present invention, FIG. 2 is an elevation view of an AI robot in FIG. 1, and FIG. 3 is a block diagram illustrating a control relationship of the AI robot in FIG. 1.

Referring to FIG. 1, the robot system according to the one embodiment of the present invention may include one or more robots 1 to provide services in various places including a home and a hospital. For example, the robot system may include an AI robot 1 which may interact with a user in a home or the like, identify the user according to a medication schedule of the user, discharge a medicine corresponding to the user, determine whether the user has taken the medicine and the user's reaction after taking the medicine, and take measures suited to a result of the determination.

Preferably, the robot system according to the one embodiment of the present invention may include a plurality of AI robots 1, and a server 2 which may manage and control the AI robots 1.

The server 2 may remotely monitor and control the states of the AI robots 1, and the robot system may provide more effective services using the robots 1.

The robots 1 and the server 2 may each include communication means (not shown) supporting one or more communication protocols to communicate with each other. In addition, the robots 1 and the server 2 may communicate with PCs, mobile terminals, and other external servers.

For example, the robots 1 and the server 2 may be implemented to wirelessly communicate using wireless communication techniques such as IEEE 802.11 WLAN, IEEE 802.15 WPAN, UWB, Wi-Fi, Zigbee, Z-wave, and Blue-Tooth. The robots 1 may use different wireless communication techniques depending on communication schemes of other devices or the server 2.

In particular, each of the robots 1 may wirelessly communicate with the other robots 1 and/or the server 2 over a 5G network. When the robots 1 wirelessly communicate over the 5G network, real-time response and real-time control may be performed.

In addition, the robots 1 and the server 2 may communicate using a Message Queuing Telemetry Transport (MQTT) scheme and a HyperText Transfer Protocol (HTTP) scheme.

Further, the robots 1 and the server 2 may communicate with PCs, mobile terminals, and other external servers in the HTTP or MQTT scheme.

In some cases, the robots 1 and the server 2 may support two or more communication protocols and use optimum communication protocols according to the type of communication data and the types of devices participating in communication.

The user may check or control information about the robots 1 in the robot system through a user terminal 3 such as a PC or a mobile terminal.

In this specification, the 'user' may be a person using a service through at least one robot, and include a personal customer purchasing or renting the robot to use the same at home or the like, a manager of a company providing a service to a staff member or customer using the robot, and customers using services provided by the staff and the company. In this regard, the 'user' may include Business to Consumer (B2C) and Business to Business (B2B).

The server 2 may be implemented with a cloud server, and the user may use data stored in the server 2 to which the user terminal 3 is communication-connected and a function and a service provided by the server 2. The cloud server 2 may be linked to the robots 1 to monitor and control the robots 1 and remotely provide various solutions and contents thereto.

The server 2 may store and manage information received from the robots 1 and other devices. The server 2 may be a server provided by the manufacturer of the robots 1 or a company to which the manufacturer commits a service. The server 2 may be a control server which manages and controls the robots 1.

The server 2 may control the robots 1 in the same manner or control the same individually. In addition, the server 2 may group at least some of the robots 1 and then control the same on a group basis.

On the other hand, the server 2 may be made up of a plurality of servers having distributed information and functions, or one integrated server.

The robots 1 and the server 2 may each include communication means (not shown) supporting one or more communication protocols to communicate with each other.

Each robot 1 may transmit space, object and usage-associated data to the server 2.

Here, the space and object-associated data may be recognition-associated data of a space and an object recognized by the robot 1 or image data of a space and an object captured by an image capture unit.

In some embodiments, the robot 1 and the server 2 may each include an Artificial Neural Network (ANN) in the form of software or hardware learned to recognize at least one of attributes of a user, a voice and a space and an attribute of an object such as an obstacle.

According to the one embodiment of the present invention, the robot 1 and the server 2 may each include a Deep Neural Network (DNN), such as a Convolutional Neural Network (CNN), a Recurrent Neural Network (RNN) or a Deep Belief Network (DBN), learned through deep learning. For example, a controller 140 of the robot 1 may be equipped with a structure of the DNN such as the CNN.

The server 2 may let the DNN learn based on data received from the robot 1, data input by the user, etc., and then transmit updated DNN structure data to the robot 1. As a result, a DNN structure of artificial intelligence provided in the robot 1 may be updated.

The usage-associated data may be data acquired according to use of the robot 1, which may include use history data, a sense signal acquired by a sensor unit 170, etc.

The learned DNN structure may receive input data for recognition, recognize attributes of a person, an object and a space included in the input data, and output the recognition result.

In addition, the learned DNN structure may receive input data for recognition, analyze and learn usage-associated data of the robot 1, and recognize a use pattern, a use environment, etc.

On the other hand, the space, object and usage-associated data may be transmitted to the server 2 through a communication unit 190.

The server 2 may let the DNN learn based on received data and then transmit updated DNN structure data to the AI robot 1 to update the same.

Accordingly, the robot 1 may become increasingly smart and provide user experience (UX) evolved whenever used. The robot 1 and the server 2 may also use external information. For example, the server 2 may synthetically use external information acquired from other linked service servers (not shown) and thus provide excellent user experience.

Further, according to the present invention, the robot 1 may first actively provide information or output a voice recommending a function or a service, so as to provide more various and active control functions to the user.

FIG. 2 illustrates an AI robot 1 capable of providing a medication service to a user.

The AI robot 1 is an AI robot capable of providing the medication service, etc. to the user, and includes a head 30 which includes a display 180a to display a certain image such as a user interface screen, a body 20 which contains medicines to be taken and discharges a desired one of the medicines under control, and a traveling unit 10 which supports the head 30 and the body 20 and travels movably.

The configurations of the head 30, body 20 and traveling unit 10 may be embodied in various ways and are not limited to FIG. 2.

The head 30 may include the display, and display a user interface (UI) screen including an event, an advertisement, medication-associated information, etc. on the display 180a. The display 180a may be configured with a touch screen and thus used as input means.

In addition, the AI robot 1 may receive a user input such as a touch or a voice input, and display information corresponding to the user input on the screen of the display 180a.

In some embodiments, the AI robot 1 may include a scanner capable of identifying a ticket, an airplane ticket, a barcode, a QR code, etc. for guidance.

The head 30 may further include a camera of an image capture unit 120.

The camera may be disposed in the head 30 to capture image data within a predetermined range of a direction in which the head 30 is directed.

For example, when the AI robot 1 searches for the user, the head 30 may be turned to be directed to the user identified by the camera.

In some embodiments, the AI robot 1 may include two displays 180a and 180b, at least one of which may be configured with a touch screen and thus used as input means.

Here, one of the two displays 180a and 180b may be disposed in the head 30 and the other one 180b may be formed in the body 20, but are not limited thereto.

This AI robot 1 may include a container (not shown) inside the body 20 supporting the head 30.

The container may be formed to have an inner space between an inlet 182 and an outlet 183, and sort out and store predetermined medicines injected through the inlet 182.

The inlet 182 and the outlet 183 may be formed at one side of the body 20 separately from each other or integrally with each other.

The traveling unit 10 may include a wheel, a motor, etc. to take charge of traveling. Alternatively, in the case where the AI robot 1 is fixed, the traveling unit 10 may function as a support region.

In the case where the traveling unit 10 advances traveling, it may include at least one slit 10a.

The slit 10a may be formed from a front portion to a side portion of the circumferential surface of the traveling module 10 such that an internal front Lidar (not shown) is operable.

The front Lidar may be disposed inside the traveling module 10 to face the slit 10a. As a result, the front Lidar may emit a laser beam through the slit 10a.

Another slit (not shown) may be formed from a rear portion to a side portion of the circumferential surface of the traveling unit 10 such that an internal rear Lidar (not shown) is operable.

The traveling unit 10 may further include another slit formed such that an internal sensor, such as a precipice sensor which senses presence/absence of a precipice on the floor within a traveling zone, is operable.

On the other hand, a sensor may also be disposed on the outer surface of the traveling unit 10. An obstacle sensor, such as an ultrasonic sensor which senses an obstacle, may be disposed on the outer surface of the traveling unit 10.

For example, the ultrasonic sensor may be a sensor which measures the distance between an obstacle and the AI robot 1 using an ultrasonic signal. The ultrasonic sensor may perform a function of sensing an obstacle in the vicinity of the AI robot 1.

This AI robot 1 may perform a given task while traveling in a specific space. The AI robot 1 may perform autonomous traveling in which the robot creates a path to a target destination and moves along the created path, and follow traveling in which the robot moves by following a person or another robot. In order to prevent accidents, the AI robot 1 may travel, while sensing and dodging obstacles while in motion based on image data captured through the image capture unit 120, sense data acquired by the sensor unit 170, etc. In detail, this AI robot 1 may provide a medication service of discharging a specific medicine stored therein to a specific user by a server or according to a specific schedule.

A modular design may be applied to the AI robot 1 to provide a service optimized according to a use environment and usage.

A description will hereinafter be given of an internal block diagram for control of the AI robot 1.

FIG. 3 is a block diagram illustrating a control relationship of the AI robot in FIG. 1.

Referring to FIG. 3, the AI robot 1 according to the one embodiment of the present invention may include the controller 140 which controls the entire operation of the AI robot 1, a storage unit 130 which stores various data, and the communication unit 190 which transmits/receives data to/from other devices including the server 2.

The controller 140 may control the storage unit 130, the communication unit 190, a driving unit 160, the sensor unit 170, an output unit 180, etc. in the AI robot 1 to control the entire operation of the AI robot 1.

The storage unit 130 may record various information necessary to control of the AI robot 1, and include a volatile or nonvolatile recording medium. The recording medium may store data readable by a microprocessor, and include a Hard Disk Drive (HDD), a Solid State Disk (SSD), a Silicon Disk Drive (SDD), a ROM, a RAM, a CD-ROM, a magnetic tape, a floppy disk, an optical data storage unit, etc.

The communication unit 190 may include at least one communication module such that the AI robot 1 is connected to the Internet or a certain network and communicates with other devices.

The communication unit 190 may also be connected with a communication module provided in the server 2 to process data transmission/reception between the AI robot 1 and the server 2.

The AI robot 1 according to the one embodiment of the present invention may further include a voice input unit 125 which receives the user's voice input through a microphone.

The voice input unit 125 may include a processor which converts an analog voice into digital data, or be connected to the processor such that the user's input voice signal is converted into data recognizable by the controller 140 or server 2.

On the other hand, the storage unit 130 may store data for voice recognition, and the controller 140 may process the user's voice input signal received through the voice input unit 125 and perform a voice recognition process.

Meanwhile, the controller 140 may perform a control operation such that the robot 1 performs a predetermined operation based on a result of the voice recognition.

On the other hand, the AI robot 1 may include an output unit 180 to display predetermined information as an image or output the same as an audio.

The output unit 180 may include displays 180a and 180b which display, as images, information corresponding to the user's command input, a process result corresponding to the user's command input, an operation mode, an operation state, an error state, etc. In some embodiments, the AI robot 1 may include a plurality of displays 180a and 180b.

In some embodiments, at least some of the displays 180a and 180b may form an interlayer structure with a touchpad to constitute a touch screen. In this case, the display 180a constituting the touch screen may be used as an input device enabling input of information by the user's touch, besides an output device.

The output unit 180 may further include an audio output unit 181 which outputs an audio signal. The audio output unit 181 may output, as audios, an alarm sound, notification messages indicative of an operation mode, an operation state, an error state, etc., information corresponding to the user's command input, a process result corresponding to the user's command input, etc. under the control of the controller 140. The audio output unit 181 may convert an electrical signal from the controller 140 into an audio signal and output the converted audio signal. To this end, the audio output unit 181 may include a speaker, etc.

In some embodiments, the AI robot 1 may further include the image capture unit 120, which may capture an image within a predetermined range.

The image capture unit 120 may capture an image around the AI robot 1, an image of an external environment, etc., and include a camera module. A plurality of cameras may be installed in various parts for capture efficiency, and be disposed in the head as stated previously.

The image capture unit 120 may capture an image for user recognition. The controller 140 may, based on an image captured by the image capture unit 120, determine an external situation or recognize the user (guide object).

In addition, in the case where the robot 1 is an AI robot, the controller 140 may perform a control operation such that the robot 1 travels based on an image captured by the image capture unit 120.

On the other hand, an image captured by the image capture unit 120 may be stored in the storage unit 130.

The AI robot 1 may further include the driving unit 160 for motion, which may move the body under the control of the controller 140.

The driving unit 160 may be disposed within the traveling unit of the robot, and include at least one driving wheel (not shown) which moves the body. The driving unit 160 may include a driving motor (not shown) connected to the driving wheel to rotate the same. The driving wheel may include driving wheels provided respectively at left and right sides of the body, which will hereinafter be referred to as a left wheel and a right wheel, respectively.

Although the left wheel and the right wheel may be driven by one driving motor, a left wheel driving motor for driving of the left wheel and a right wheel driving motor for driving of the right wheel may be individually provided as needed. The traveling direction of the body may be turned to the left or right by making the rotation speeds of the left wheel and right wheel different.

On the other hand, the AI robot 1 may include the sensor unit 110, which includes sensors for sensing various data related to the operation and state of the AI robot 1.

The sensor unit 110 may further include an operation sensor which senses the operation of the robot 1 and outputs operation information. For example, the operation sensor may be a gyro sensor, a wheel sensor, an acceleration sensor, or the like.

The sensor unit 170 may include an obstacle sensor for sensing an obstacle, which may include an infrared sensor, an ultrasonic sensor, an RF sensor, a geomagnetic sensor, a Position Sensitive Device (PSD) sensor, a precipice sensor which senses presence/absence of a precipice on the floor within a traveling zone, a light detection and ranging (Lidar), etc.

On the other hand, the obstacle sensor senses an object, more particularly, an obstacle, existing in a traveling (moving) direction of the AI robot and transfers obstacle information to the controller 140. At this time, the controller 140 may control the motion of the AI robot 1 according to the position of the sensed obstacle.

Meanwhile, the controller 140 may perform a control operation such that the operation state of the AI robot 1, a user input, or the like is transmitted to the server 2, etc. through the communication unit 190.

Upon receiving a medication command from the server or according to a predetermined schedule, this controller 140 acquires a surrounding image for searching for a user and determines based on image data whether the user is a target of the current medication schedule.

At this time, if the user is specified, the controller 140 discharges and provides a corresponding medicine to the user. The controller 140 may also read an image from the image capture unit and determine based on the read image whether the user has taken the discharged medicine.

In addition, the controller 140 may determine the state of the user based on an image about the state of the user after medicine-taking and a sense signal from a sensor, and perform a service such as an alarm or an emergency measure according to a result of the determination.

The controller 140 may perform user identification and user action determination from the above image data and sense signal through a computer vision system.

Hereinafter, a healthcare method of the AI robot 1 will be described in detail with reference to FIGS. 4 to 6.

Figure 4:
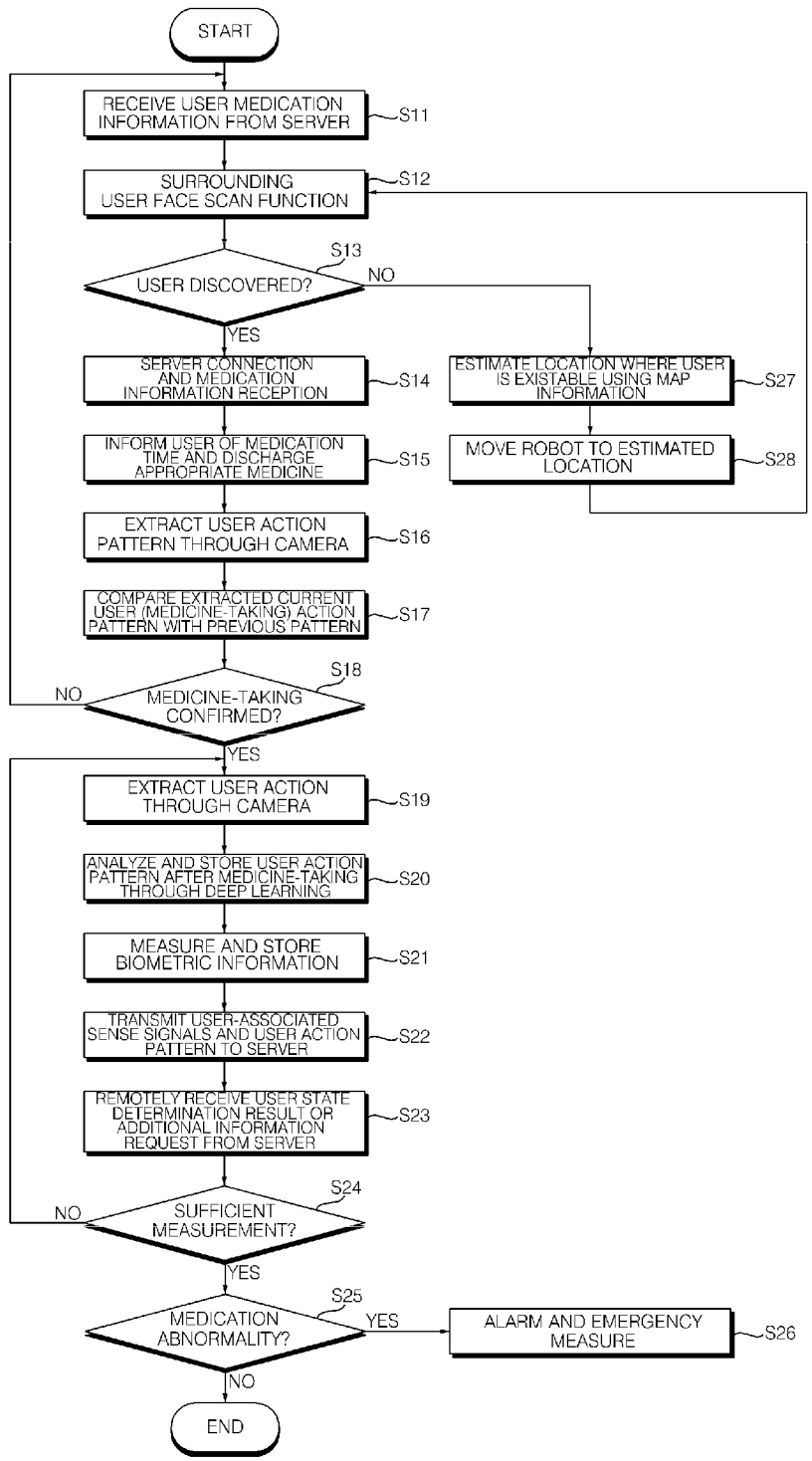
FIG. 4 is a flowchart illustrating a medication service control method according to a first scenario of the AI robot in FIG. 1.
Figure 5:
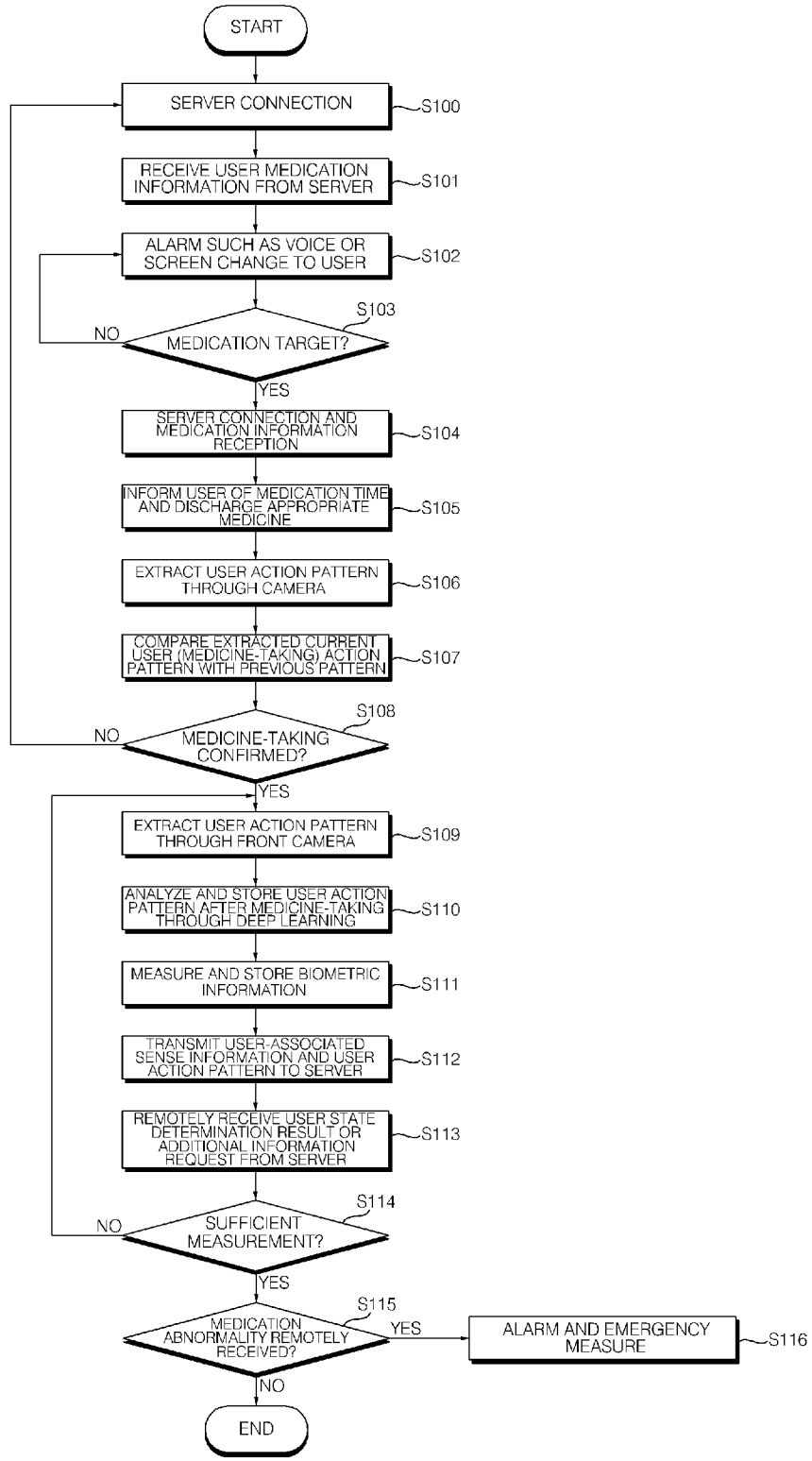
FIG. 5 is a flowchart illustrating a medication service control method according to a second scenario of the AI robot in FIG. 1.
Figure 6:
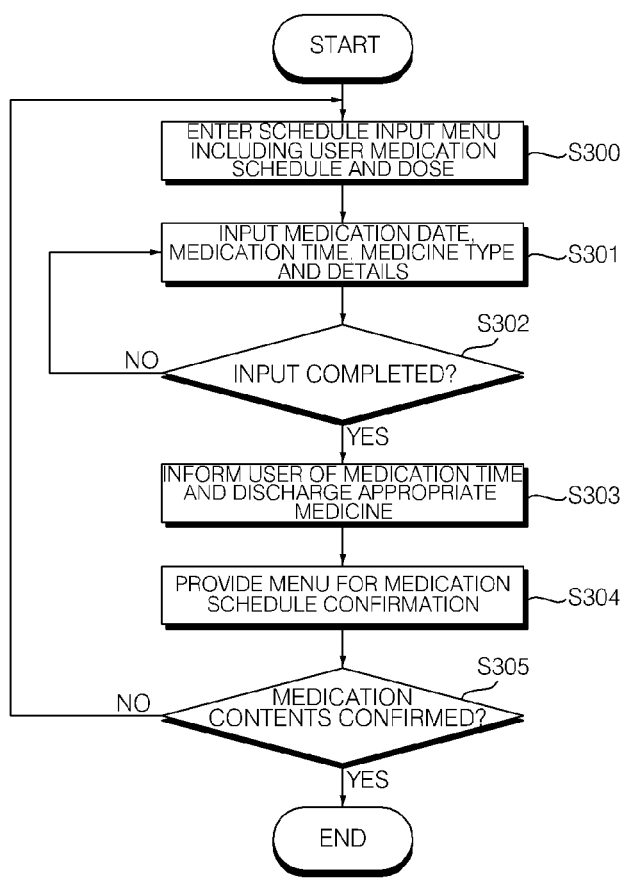
FIG. 6 is a flowchart illustrating a medication information input scenario of the AI robot in FIG. 1.

FIG. 4 is a flowchart illustrating a medication service control method according to a first scenario of the AI robot in FIG. 1, FIG. 5 is a flowchart illustrating a healthcare method according to a second scenario of the AI robot in FIG. 1, and FIG. 6 is a flowchart illustrating a medication information input scenario of the AI robot in FIG. 1.

First, the AI robot 1 receives information about a medication service from the server 2 (S11).

Namely, the AI robot 1 receives a medication command and medication information from the server 2 according to a medication schedule of a specific user.

The medication information may include information about a medication target of the current medication schedule, information about the type of a specific medicine to be taken, information about a medication method, etc.

The controller 140 of the AI robot 1 scans the face of a discovered user based on the received medication information while the robot travels around, to determine whether the specific user is present around the robot (S12).

That is, the controller 140 acquires a surrounding image from the image capture unit 120, grasps a feature point of the exterior appearance of a discovered user when the user is present in image data, compares the feature point of the exterior appearance of the user with the medication target information, and determines based on a result of the comparison whether the discovered user is the medication target.

A computer vision system using Simulation Language for Alternative Modeling (SLAM) may be utilized for such user matching.

If the discovered user is determined to be the medication target, the AI robot 1 establishes a connection to the server 2 and receives medication information of the medication target from the server 2 (S14).

At this time, the received medication information may include information about medication execution of the previous cycle, etc.

Next, the AI robot 1 moves in front of the discovered user, informs the user that an appropriate medication time has arrived, and discharges an appropriate medicine (S15).

This medicine discharge may be performed by discharging a specific medicine through the outlet 183 according to the medication information.

Next, the controller 140 acquires image data extracted through the camera from the image capture unit 120, analyzes the image data, and then extracts an action pattern of the user (S16).

Then, the controller 140 defines the extracted current user action pattern, reads an action pattern in the medication execution of the previous cycle from the medication information of the user, and determines whether the action pattern of the current cycle is beyond the action pattern of the previous cycle (S17).

This action pattern comparison may be performed by comparing images of a medicine-taking action of the user in the current medication cycle with images of the medicine-taking action of the user in the previous medication cycle to determine whether the user has accurately performed medicine-taking in the current cycle.

Upon determining that the user has accurately performed medicine-taking in the current cycle (S18), the controller 140 acquires image data of the user through the camera (S19).

The controller 140 may extract an action of the user after medicine-taking through the acquired image data.

At this time, the controller 140 checks whether the user takes an action such as flopping down, falling down or staggering after medicine-taking, analyzes such a pattern through keywords and deep learning, and stores a result of the analysis (S20).

In addition, the controller 140 may measure biometric information of the user through the sensor units 170 and acquire the resulting sense signal (S21).

This biometric information sense signal may be a sense signal about a temperature variation, heartbeat or the like of the user.

Then, the sense signals about the action pattern and biometric information of the user may be transmitted to the server 2 (S22). Then, the server 2 may store received information in a database for utilization as comparative data in the next cycle, determine the state of the user after medicine-taking based on the received information, and transmit a command based on a result of the determination to the AI robot 1 (S23).

Next, when the AI robot 1 remotely receives the determination result of the user's state or an additional information request from the server 2, it may determine whether additional information of the user can be provided (S24). That is, the AI robot 1 may again determine whether the measurement of biometric information sufficient to determine the user's state has been made.

Upon determining that the sufficient biometric information measurement has been made, the AI robot 1 determines whether information about a determination that the user is abnormal due to medication is received from the server 2 (S25).

When the AI robot 1 receives a command about medication abnormality of the user from the server 2, it generates an alarm and performs operations for an emergency measure, etc. (S26).

Namely, the AI robot analyzes image data of the user after medicine-taking, stores a result of the analysis, transmits the stored analysis result to the server 2, measures biometric information of the user, and transfers the resulting information to the server 2. In this case, for example, upon determining through the image data that the user flops down and determining through the biometric information that the user's temperature suddenly rises, the server 2 may determine that the current situation requires an alarm and an emergency measure, and transmit a result of the determination to the AI robot.

As a result, the AI robot 1 may generate a voice or siren alarm to inform surrounding persons that the user is abnormal. In addition, the AI robot 1 may operate an emergency communication network associated with the emergency situation to call a linked hospital, emergency center or the like for help.

On the other hand, unless the specific user is discovered while scanning surrounding persons, the AI robot 1 may estimate a location where the user is existable, using map information of the traveling zone (S27).

At this time, in the location estimation, the user location may be estimated on the basis of main user locations from the medication information of the previous cycle.

The AI robot 1 may move to the estimated location to again determine whether the specific user is present (S28).

In this manner, upon receiving a medication service execution command based on a medication schedule from the server 2, the AI robot 1 acquires surrounding image data, and analyzes the image data to perform user identification, medicine-taking check, user state check after medicine-taking, etc., so as to actively and properly cope with the medication.

Therefore, the AI robot may check whether the medicine-taking has been completely performed and check the state of the user after the medicine-taking, thereby making it possible to actively and properly cope with user abnormality resulting from an ill effect, etc.

On the other hand, in the case where the AI robot 1 is a fixed robot which does not include the traveling unit 10, it may provide a medication service as in FIG. 5.

First, once the AI robot 1 begins to operate under the condition of being connected to the server 2 (S100), it receives a medication command and medication information from the server 2 according to a medication schedule of a user (S101).

The medication information may include information about a medication target of the current medication schedule, information about the type of a specific medicine to be taken, information about a medication method, etc.

The controller 140 of the AI robot 1 generates an alarm such as a voice or screen change to a surrounding user to inform the user that a medication cycle has arrived (S102).

Here, the voice alarm may be a predetermined notification sound, which may be a guide announcement such as "Mr. 000, it is time to take your medicine.".

When the surrounding user moves in front of the camera of the AI robot 1 owing to such an alarm, the camera captures an image of the user for determination as to whether the user is the medication target in the current cycle (S103).

That is, the controller 140 acquires a surrounding image from the image capture unit 120, grasps a feature point of the exterior appearance of a discovered user when the user is present in image data, compares the feature point of the exterior appearance of the user with the medication target information, and determines based on a result of the comparison whether the discovered user is the medication target. A computer vision system using SLAM may be utilized for such user matching.

If the discovered user is determined to be the medication target, the AI robot 1 establishes a connection to the server 2 and receives medication information of the medication target from the server 2 (S104).

At this time, the received medication information may include information about medication execution of the previous cycle, etc.

Next, the AI robot 1 moves in front of the discovered user, informs the user of an appropriate medication time, and discharges an appropriate medicine (S105).

This medicine discharge may be performed by discharging a specific medicine through the outlet 183 according to the medication information.

Next, the controller 140 acquires image data extracted through the camera from the image capture unit 120, analyzes the image data, and then extracts an action pattern of the user (S106).

Then, the controller 140 defines the extracted current user action pattern, reads an action pattern in the previous medication execution from the medication information of the user, and determines whether the current action pattern is beyond the previous action pattern (S107).

This action pattern comparison may be performed by comparing images of a medicine-taking action of the user in the current medication cycle with images of the medicine-taking action of the user in the previous medication cycle to determine whether the user has accurately performed medicine-taking in the current cycle.

Upon determining that the user has accurately performed medicine-taking in the current cycle (S108), the controller 140 acquires image data of the user through the camera.

The controller 140 may extract an action of the user after medicine-taking through the acquired image data (S109).

At this time, the controller 140 checks whether the user takes an action such as flopping down, falling down or staggering after medicine-taking, analyzes such a pattern through keywords and deep learning, and stores a result of the analysis (S110).

In addition, the controller 140 may measure biometric information of the user through the sensor units 170 and acquire the resulting sense signal (S111).

This biometric information sense signal may be an acquired sense signal about a temperature variation, heartbeat or the like of the user.

Then, the sense signals about the action pattern and biometric information of the user may be transmitted to the server 2 (S112). Then, the server 2 may store received information in a database for utilization as comparative data in the next cycle, determine the state of the user after medicine-taking based on the received information, and transmit a command based on a result of the determination to the AI robot 1.

Next, when the AI robot 1 remotely receives the determination result of the user's state or an additional information request from the server 2, it may determine whether additional information of the user can be provided. That is, the AI robot 1 may again determine whether the measurement of biometric information sufficient to determine the user's state has been made (S113).

Upon determining that the sufficient biometric information measurement has been made (S114), the AI robot 1 determines whether the server 2 remotely determines that the user is abnormal due to medication.

When the AI robot 1 receives a command about medication abnormality of the user from the server 2 (S115), it generates an alarm and performs operations for an emergency measure, etc. (S116).

Namely, the AI robot analyzes image data of the user after medicine-taking, stores a result of the analysis, transmits the stored analysis result to the server 2, measures biometric information of the user, and transfers the resulting information to the server 2. In this case, for example, upon determining through the image data that the user flops down and determining through the biometric information that the user's temperature suddenly rises, the server 2 may determine that the current situation requires an alarm and an emergency measure, and transmit a result of the determination to the AI robot.

As a result, the AI robot 1 may generate a voice or siren alarm to inform surrounding persons that the user is abnormal. In addition, the AI robot 1 may operate an emergency communication network associated with the emergency situation to call a linked hospital, emergency center or the like for help.

In this manner, upon receiving a medication service execution command based on a medication schedule from the server 2, the AI robot 1 acquires surrounding image data, and analyzes the image data to perform user identification, medicine-taking check, user state check after medicine-taking, etc., so as to actively and properly cope with the medication.

On the other hand, the AI robot 1 may receive a medication schedule directly from a user and provide a medication service according to the received schedule.

Namely, the AI robot 1 may directly receive information about a medication schedule of a specific user from a user, as in FIG. 6.

First, when the user selects a schedule input icon on the display 180a of the AI robot 1 to enter a schedule input menu (S300), the controller 140 changes the current mode to a medication schedule input mode and displays a request list for a schedule to be received.

That is, the controller 140 may display a request list for user information, a medication date, a medication time, a medication cycle, a medicine type, guide contents, etc. on the display.

The user may input corresponding information in the displayed request list (S301).

When the AI robot 1 receives the corresponding information, the controller 140 stores settings based on the corresponding information in the storage unit 130 and performs matching with the user information. Here, the user information may be image data received through user photographing or the like. Alternatively, the user information may be personal information or a personal password set and input (S302).

For example, in the case of input of a medication schedule for a specific medicine, 08:00, 14:00 and 21:00 daily for thirty days after medicine-taking start on a start date, for example, May 1, 2019 may be input as medication times. At this time, the type of the medicine may be entered in detail.

When this medication schedule information is received, the user information is received and the matching with the user information is finished, the controller 140 determines that the input of the medication schedule has been completed, stores the medication schedule information in the storage unit 130, and performs the medication service according to the schedule.

That is, when the first time of the set start date has arrived, the AI robot 1 searches for a user, determines that the searched user is a medication target, informs the user of the medication time, and discharges a corresponding medicine to invite the user to take the medicine, as described with reference to FIG. 4 (S303).

At this time, the AI robot may provide the user with a menu for medication schedule confirmation, namely, provide the user with a confirm button for asking the user whether he/she has taken the medicine, and urge medication completion by inviting the user to push the confirm button (S304).

In addition, as in FIGS. 4 and 5, the AI robot may analyze the image of the user to confirm the medicine-taking fact, and, if the medicine-taking is completed, read the subsequent image of the user to determine presence/absence of abnormality in the user.

In this manner, the AI robot 1 may receive a medication schedule directly from a user and provide a medication service according to the received schedule, thereby making it possible to individually provide the medication service within the traveling zone separately from the external server 2.

Hereinafter, with reference to FIGS. 7 and 8, a description will be given of a medication service which is individually provided within the traveling zone separately from the server 2.

Figure 7:
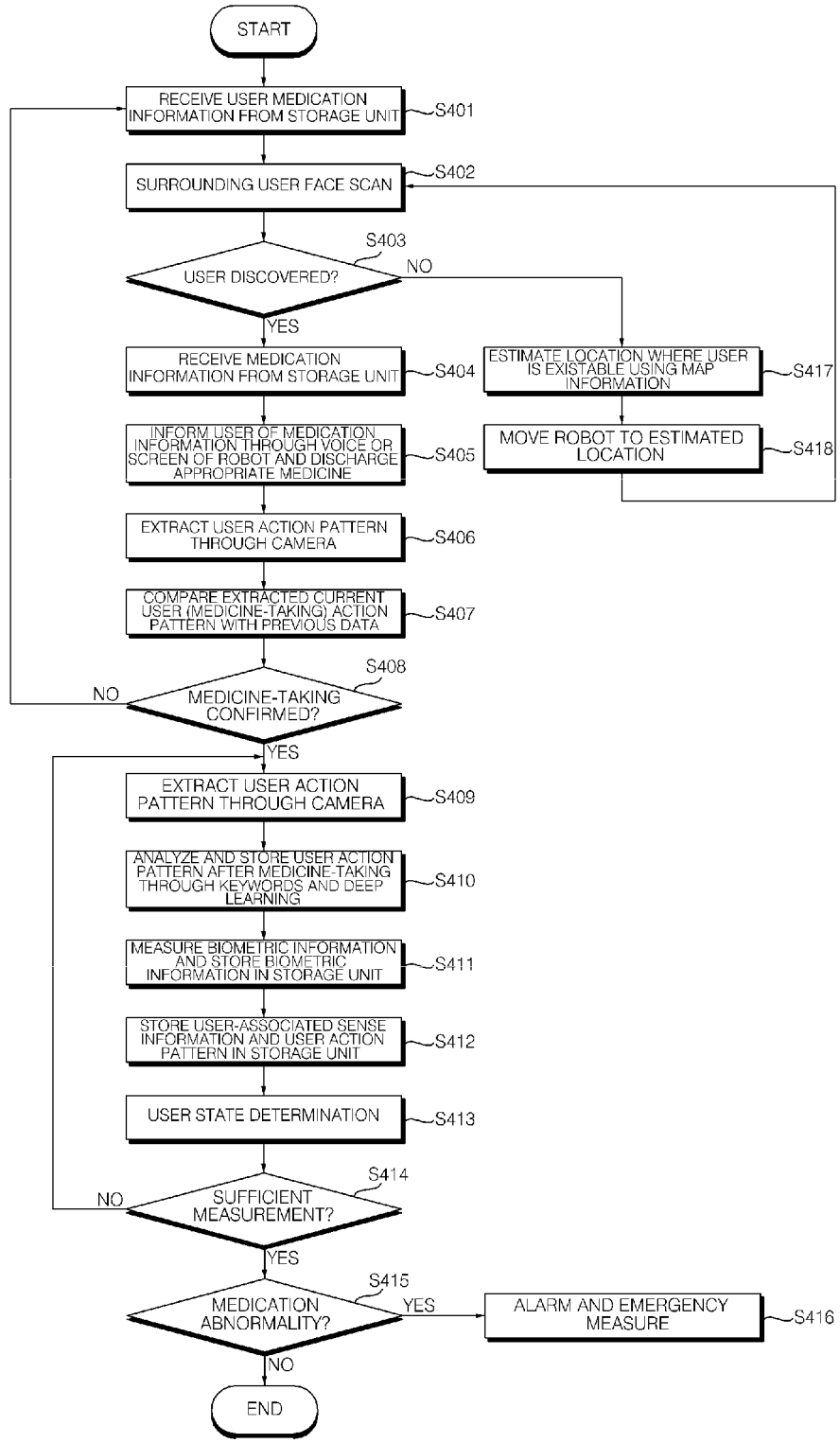
FIG. 7 is a flowchart illustrating a medication service control method according to a third scenario of the AI robot in FIG. 1.

FIG. 7 is a flowchart illustrating a medication service control method according to a third scenario of the AI robot 1 in FIG. 1.

In detail, once the AI robot 1 begins to operate according to the medication schedule set as in FIG. 6, the AI robot 1 reads medication information of a specific user from the storage unit 130 (S401).

The medication information may include information about a medication target of the current medication schedule, information about the type of a specific medicine to be taken, information about a medication method, etc.

The controller 140 of the AI robot 1 scans the face of a discovered user based on the received medication information while the robot travels around, to determine whether the specific user is present around the robot (S402).

That is, the controller 140 acquires a surrounding image from the image capture unit 120, grasps a feature point of the exterior appearance of a discovered user when the user is present in image data, compares the feature point of the exterior appearance of the user with the medication target information, and determines based on a result of the comparison whether the discovered user is the medication target. A computer vision system using SLAM may be utilized for such user matching (S403).

If the discovered user is determined to be the medication target, the AI robot 1 establishes a connection to the server 2 and receives medication information of the medication target from the server 2 (S404).

At this time, the received medication information may include information about medication execution of the previous cycle, etc.

Next, the AI robot 1 moves in front of the discovered user, informs the user of an appropriate medication time, and discharges an appropriate medicine (S405).

This medicine discharge may be performed by discharging a specific medicine through the outlet 183 according to the medication information.

Next, the controller 140 acquires image data extracted through the camera from the image capture unit 120, analyzes the image data, and then extracts an action pattern of the user (S406).

Then, the controller 140 defines the extracted current user action pattern, reads an action pattern in the previous medication execution from the medication information of the user, and determines whether the current action pattern is beyond the previous action pattern (S407).

This action pattern comparison may be performed by comparing images of a medicine-taking action of the user in the current medication cycle with images of the medicine-taking action of the user in the previous medication cycle to determine whether the user has accurately performed medicine-taking in the current cycle (S408).

Upon determining that the user has accurately performed medicine-taking in the current cycle, the controller 140 acquires image data of the user through the camera (S409).

The controller 140 may extract an action of the user after medicine-taking through the acquired image data.

At this time, the controller 140 checks whether the user takes an action such as flopping down, falling down or staggering after medicine-taking, analyzes such a pattern through keywords and deep learning, and stores a result of the analysis (S410).

In addition, the controller 140 may measure biometric information of the user through the sensor units 170 and acquire the resulting sense signal (S411). This biometric information sense signal may be an acquired sense signal about a temperature variation, heartbeat or the like of the user.

Then, the sense signals about the action pattern and biometric information of the user may be stored in the storage unit 130 (S412). The controller 140 may utilize the sense signals about the action pattern and biometric information of the current cycle stored in the storage unit 130 as comparative data in the next cycle.

Next, the controller 140 determines the state of the user through deep learning (S413). At this time, the controller 140 may again determine whether the measurement of biometric information sufficient to determine the user's state has been made (S414).

Upon determining that the sufficient biometric information measurement has been made, the AI robot 1 finally determines whether the user is abnormal due to medication (S415).

Upon determining that the user is abnormal due to medication, the AI robot 1 generates an alarm and performs operations for an emergency measure, etc. (S416).

Namely, the AI robot analyzes image data of the user after medicine-taking, stores a result of the analysis, and measures biometric information of the user. In this case, for example, upon determining through the image data that the user flops down and determining through the biometric information that the user's temperature suddenly rises, the AI robot may determine that the current situation requires an alarm and an emergency measure.

As a result, the AI robot 1 may generate a voice or siren alarm to inform surrounding persons that the user is abnormal. In addition, the AI robot 1 may operate an emergency communication network associated with the emergency situation to call a linked hospital, emergency center or the like for help.

On the other hand, unless the specific user is discovered while scanning surrounding persons, the AI robot 1 may estimate a location where the user is existable, using map information of the traveling zone (S417).

At this time, in the location estimation, the user location may be estimated on the basis of main user locations from the previous medication information.

The AI robot 1 may move to the estimated location to again determine whether the specific user is present (S418).

In this manner, upon receiving a medication service execution command based on a preset medication schedule, the AI robot 1 acquires surrounding image data, and analyzes the image data to perform user identification, medicine-taking check, user state check after medicine-taking, etc., so as to actively and properly cope with the medication.

Therefore, the AI robot may check whether the medicine-taking has been completely performed and check the state of the user after the medicine-taking, thereby making it possible to actively and properly cope with user abnormality resulting from an ill effect, etc.

Figure 8:
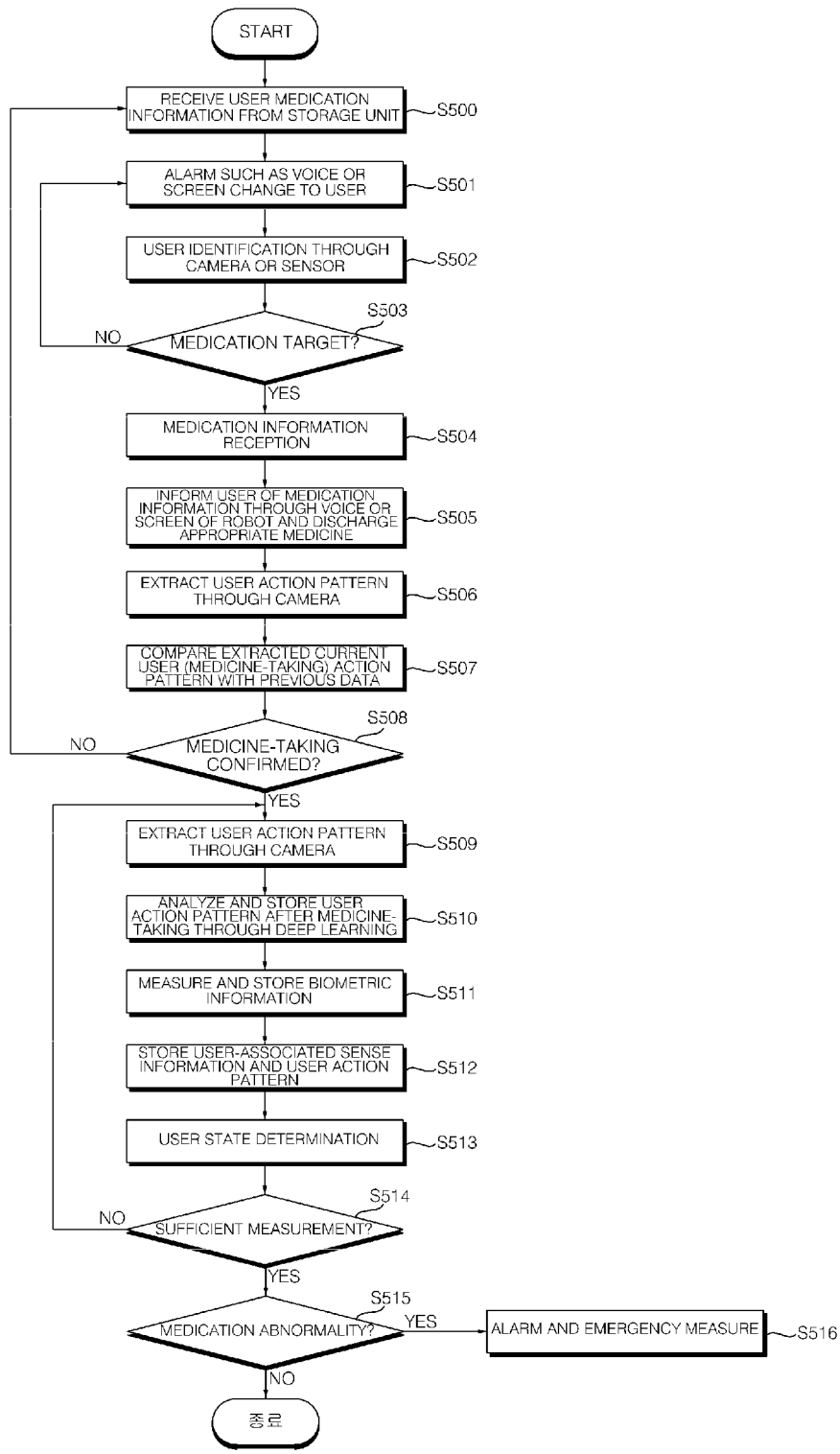
FIG. 8 is a flowchart illustrating a medication service control method according to a fourth scenario of the AI robot in FIG. 1.

FIG. 8 is a flowchart illustrating a medication service control method according to a fourth scenario of the AI robot 1 in FIG. 1.

Even in the case where the AI robot 1 is a fixed robot 1 which does not include the traveling unit 10, it may receive information about a medication schedule from a user without being connected to the server, as in FIG. 6, and independently provide a service within the traveling zone.

Once the AI robot 1 begins to operate, it reads medication information from the storage unit 130 according to a medication schedule of a user (S500).

The medication information may include information about a medication target of the current medication schedule, information about the type of a specific medicine to be taken, information about a medication method, etc.

The controller 140 of the AI robot 1 generates an alarm such as a voice or screen change to a surrounding user to inform the user that a medication cycle has arrived (S501).

Here, the voice alarm may be a predetermined reception sound, which may be a guide announcement such as "Mr. 000, it is time to take your medicine.".

When the surrounding user moves in front of the camera of the AI robot 1 owing to such an alarm, the camera captures an image of the user for determination as to whether the user is the medication target in the current cycle (S502).

That is, the controller 140 acquires a surrounding image from the image capture unit 120, grasps a feature point of the exterior appearance of a discovered user when the user is present in image data, compares the feature point of the exterior appearance of the user with the medication target information, and determines based on a result of the comparison whether the discovered user is the medication target. A computer vision system using SLAM may be utilized for such user matching.

If the discovered user is determined to be the medication target, the AI robot 1 receives medication information of the medication target from the storage unit 130 (S504). At this time, the received medication information may include information about medication execution of the previous cycle, etc.

Next, the AI robot 1 moves in front of the discovered user, informs the user of an appropriate medication time, and discharges an appropriate medicine (S505).

Next, the controller 140 acquires image data extracted through the camera from the image capture unit 120, analyzes the image data, and then extracts an action pattern of the user (S506). Then, the controller 140 defines the extracted current user action pattern, reads an action pattern in the previous medication execution from the medication information of the user, and determines whether the current action pattern is beyond the previous action pattern.

This action pattern comparison may be performed by comparing images of a medicine-taking action of the user in the current medication cycle with images of the medicine-taking action of the user in the previous medication cycle to determine whether the user has accurately performed medicine-taking in the current cycle (S507).

Upon determining that the user has accurately performed medicine-taking in the current cycle (S508), the controller 140 acquires image data of the user through the camera (S509). The controller 140 may extract an action of the user after medicine-taking through the acquired image data.

At this time, the controller 140 checks whether the user takes an action such as flopping down, falling down or staggering after medicine-taking, analyzes such a pattern through keywords and deep learning, and stores a result of the analysis (S510).

In addition, the controller 140 may measure biometric information of the user through the sensor units 170 and acquire the resulting sense signal (S511). This biometric information sense signal may be an acquired sense signal about a temperature variation, heartbeat or the like of the user.

Then, the sense signals about the action pattern and biometric information of the user may be stored in the storage unit 130 (S512). The controller 140 may utilize the sense signals about the action pattern and biometric information of the current cycle stored in the storage unit 130 as comparative data in the next cycle.

Next, the controller 140 determines the state of the user through deep learning (S513). At this time, the controller 140 may again determine whether the measurement of biometric information sufficient to determine the user's state has been made (S514).

Upon determining that the sufficient biometric information measurement has been made, the AI robot 1 finally determines whether the user is abnormal due to medication (S515).

Upon determining that the user is abnormal due to medication, the AI robot 1 generates an alarm and performs operations for an emergency measure, etc. (S516).

Namely, the AI robot analyzes image data of the user after medicine-taking, stores a result of the analysis, and measures biometric information of the user. In this case, for example, upon determining through the image data that the user flops down and determining through the biometric information that the user's temperature suddenly rises, the AI robot may determine that the current situation requires an alarm and an emergency measure.

Accordingly, the AI robot 1 may generate a voice or siren alarm to inform surrounding persons that the user is abnormal. In addition, the AI robot 1 may operate an emergency communication network associated with the emergency situation to call a linked hospital, emergency center or the like for help.

Figure 9:
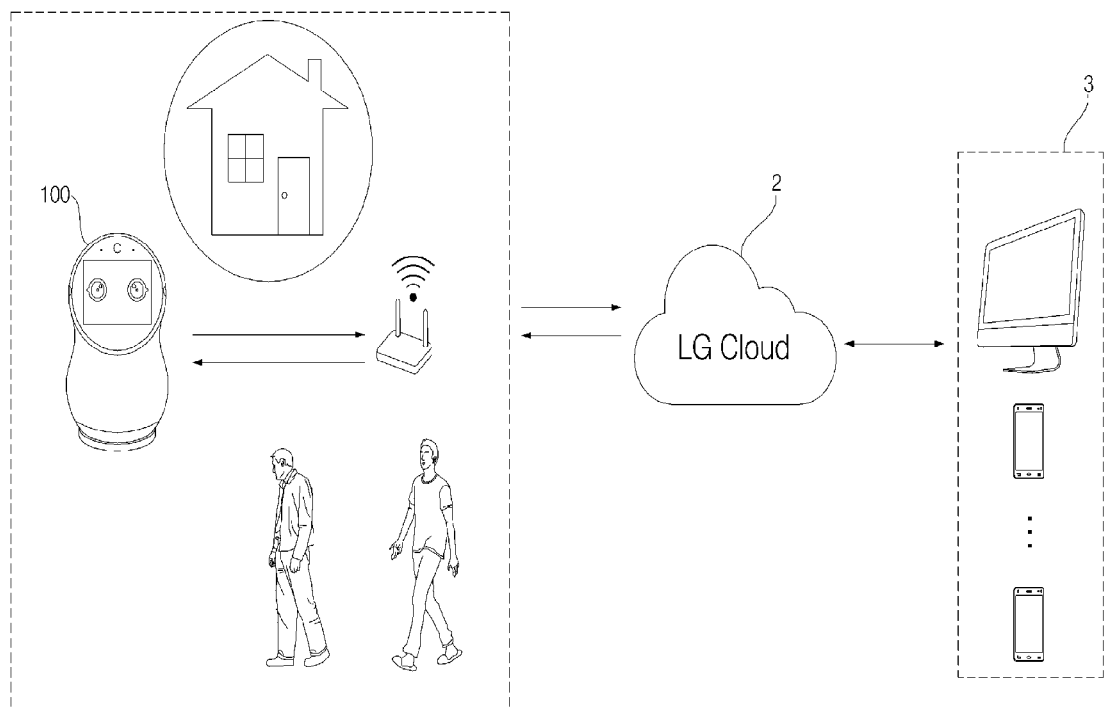
FIG. 9 is a view showing the configuration of an AI robot system according to another embodiment of the present invention.

On the other hand, a description will be given of an AI robot 1 system which provides a medication service according to another embodiment of the present invention. FIG. 9 is a view showing the configuration of the AI robot system according to the other embodiment of the present invention, and FIG. 10 is a front view of a home robot 100 in FIG. 9.

Figure 10:
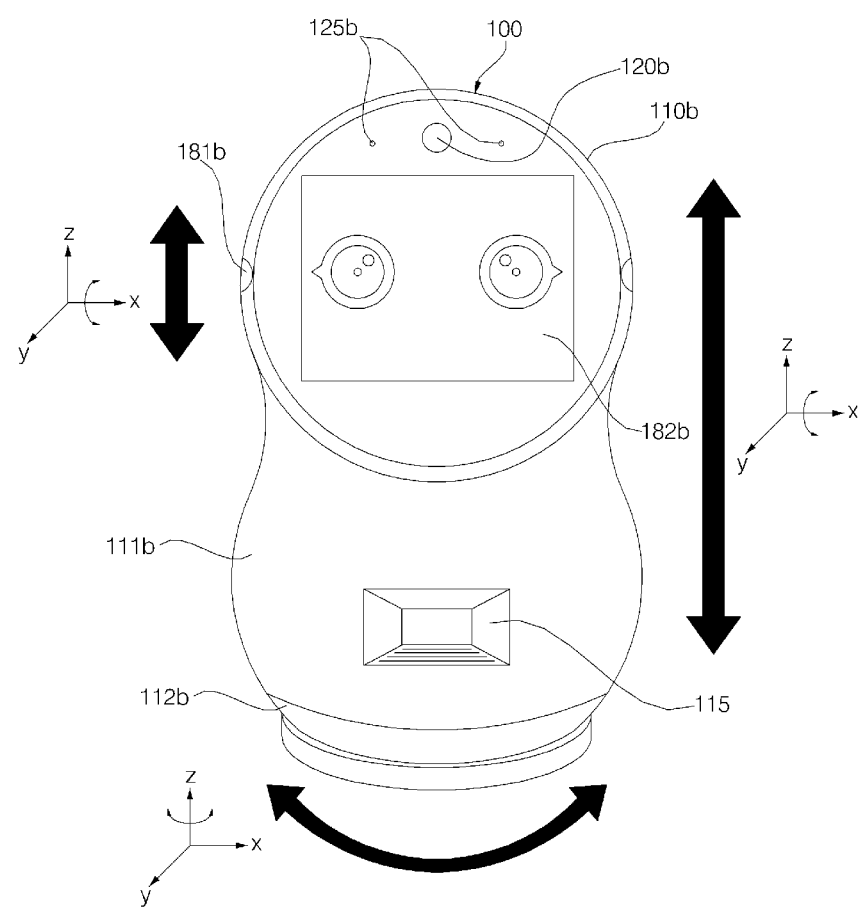
FIG. 10 is a front view of a home robot in FIG. 9.

Referring to FIGS. 9 and 10, the robot system according to the other embodiment of the present invention may include one or more robots 100 to provide services in prescribed places such as homes. For example, the robot system may include a home robot 100 which may interact with a user in a home or the like and provide various entertainment functions to the user. In addition, this home robot 100 may identify the user according to a medication schedule of the user, discharge a medicine corresponding to the user, determine whether the user has taken the medicine and the user's reaction after taking the medicine, and take measures suited to a result of the determination.

Preferably, the robot system according to the other embodiment of the present invention may include a plurality of AI robots 100, and a server 2 which may manage and control the AI robots 100.

The robots 100 and the server 2 may each include communication means (not shown) supporting one or more communication protocols to communicate with each other. In addition, the robots 100 and the server 2 may communicate with PCs, mobile terminals, and other external servers 2.

For example, the robots 100 and the server 2 may be implemented to wirelessly communicate using wireless communication techniques such as IEEE 802.11 WLAN, IEEE 802.15 WPAN, UWB, Wi-Fi, Zigbee, Z-wave, and Blue-Tooth. The robots 100 may use different wireless communication techniques depending on communication schemes of other devices or the server 2.

In particular, each of the robots 100 may wirelessly communicate with the other robots 100 and/or the server 2 over a 5G network. When the robots 100 wirelessly communicate over the 5G network, real-time response and real-time control may be performed.

The user may check or control information about the robots 100 in the robot system through a user terminal 3 such as a PC or a mobile terminal.

The server 2 may be implemented with a cloud server 2, and the user may use data stored in the server 2 to which the user terminal 3 is communication-connected and a function and a service provided by the server 2. The cloud server 2 may be linked to the robots 100 to monitor and control the robots 100 and remotely provide various solutions and contents thereto.

The server 2 may store and manage information received from the robots 100 and other devices. The server 2 may be a server 2 provided by the manufacturer of the robots 100 or a company to which the manufacturer commits a service. The server 2 may be a control server 2 which manages and controls the robots 100.

The server 2 may control the robots 100 in the same manner or control the same individually.

As described with reference to FIG. 1, each robot 100 and the server 2 may each include an Artificial Neural Network (ANN) in the form of software or hardware learned to recognize at least one of attributes of a user, a voice and a space and an attribute of an object such as an obstacle.

According to the other embodiment of the present invention, the robot 100 and the server 2 may each include a Deep Neural Network (DNN), such as a Convolutional Neural Network (CNN), a Recurrent Neural Network (RNN) or a Deep Belief Network (DBN), learned through deep learning. For example, a controller 140 of the robot 100 may be equipped with a structure of the DNN such as the CNN.

The server 2 may let the DNN learn based on data received from the robot 100, data input by the user, etc., and then transmit updated DNN structure data to the robot 100. As a result, a DNN structure of artificial intelligence provided in the robot 100 may be updated.

The learned DNN structure may receive input data for recognition, recognize attributes of a person, an object and a space included in the input data, and output the recognition result.

In addition, the learned DNN structure may receive input data for recognition, analyze and learn usage-associated data of the robot 100, and recognize a use pattern, a use environment, etc.

The server 2 may let the DNN learn based on received data and then transmit updated DNN structure data to the AI robot 100 to update the same.

Accordingly, the robot 100 may become increasingly smart and provide user experience (UX) evolved whenever used.

The home robot 100 and the server 2 may also use external information. For example, the server 2 may synthetically use external information acquired from other linked service servers 2 (not shown) and thus provide excellent user experience.

Further, according to the present invention, the robot 100 may first actively provide information or output a voice recommending a function or a service, so as to provide more various and active control functions to the user.

FIG. 10 is a front view showing the exterior appearance of a home robot 100 capable of providing a medication service to a user.

Referring to FIG. 10, the home robot 100 includes a body unit (111*b* and 112*b*) which defines the exterior appearance of the home robot 100 and contains a variety of components therein.

The body unit (111*b* and 112*b*) may include a body 111*b* having a space defined to contain a variety of components constituting the home robot 100, and a support 112*b* disposed beneath the body 111*b* to support the body 111*b*.

A container may be formed inside the body unit to store medicines.

In addition, an inlet/outlet port 115 may be formed on the outer surface of the body unit to, therethrough, inject medicines to be stored and/or discharge medicines stored.

The home robot 100 may further include a head 110*b* disposed on the body unit (111*b* and 112*b*). A display 182*b* capable of displaying an image may be disposed on the front surface of the head 110*b*.

In this specification, the forward direction may be a +y-axis direction, the upward-and-downward direction may be a z-axis direction, and the leftward-and-rightward direction may be an x-axis direction.

The head 110b may rotate within a predetermined angular range about the x-axis.

Thus, when viewed from the front, the head 110b may perform a nodding operation of moving in the upward-and-downward direction like a person who nods his/her head in the upward-and-downward direction. For example, the head 110b may perform an operation of returning to the original position after rotating within a predetermined range once or more like a person who nods his/her head in the upward-and-downward direction.

Meanwhile, in some embodiments, at least a portion of the front surface of the head 110b, on which the display 182b corresponding to the face of a person is disposed, may be configured to nod.

As such, the present embodiment is described in connection with a configuration in which the entire head 110b moves in the upward-and-downward direction. However, unless specifically stated, the nodding operation of the head 110b in the upward-and-downward direction may be substituted with an operation in which at least a portion of the front surface on which the display 182 is disposed nods in the upward-and-downward direction.

The body 111b may be configured to be rotatable in the leftward-and-rightward direction. That is, the body 111b may be configured to be rotatable 360 degrees about the z-axis.

In some embodiments, the body 111b may also be configured to be rotatable within a predetermined angular range about the x-axis, so that it may move in the upward-and-downward direction like nodding. In this case, as the body 111b rotates in the upward-and-downward direction, the head 110b may also rotate together about the axis about which the body 111b rotates.

On the other hand, the home robot 100 may include an image capture unit 120, which is capable of capturing an image of the surroundings of the body unit (111b and 112b) or at least a region within a predetermined range with respect to the front surface of the body unit (111b and 112b).

The image capture unit 120 may capture an image around the body unit (111b and 112b), an image of an external environment, etc., and include a camera module. A plurality of cameras may be installed in various parts for capture efficiency. Preferably, the image capture unit 120 may include a front camera which is provided on the front surface of the head 110b to capture a forward image of the body unit (111b and 112b).

The home robot 100 may further include a voice input unit 125b which receives the user's voice input.

The voice input unit 125b may include a processor which converts an analog voice into digital data, or be connected to the processor such that the user's input voice signal is converted into data recognizable by the server 2 or controller 140.

The voice input unit 125b may include a plurality of microphones to increase the accuracy of reception of the voice input by the user and determine the location of the user.

For example, the voice input unit 125b may include at least two microphones.

A plurality of microphones (MICs) may be disposed at different positions to be spaced apart from each other, and may acquire an external audio signal including a voice signal and convert the same into an electrical signal.

In order to estimate the direction of a sound source generating sound or the direction of the user, at least two microphones, which are input devices, are required. As the distance between the microphones increases, the resolution (angle) of direction detection becomes higher. In some embodiments, two microphones may be disposed on the head 110b. Further, two additional microphones may be provided on the rear surface of the head 110b, thereby enabling determination of the location of the user in three-dimensional space.

Further, audio output units 181b may be disposed at the left and right sides of the head 110b to output predetermined information as audios.

The exterior appearance and structure of the robot 100 shown in FIG. 10 are merely illustrative, and the present invention is not limited thereto. For example, unlike the rotation direction of the robot 100 illustrated in FIG. 10, the entire robot 100 may be inclined in a specific direction or may be shaken.

Figure 11:
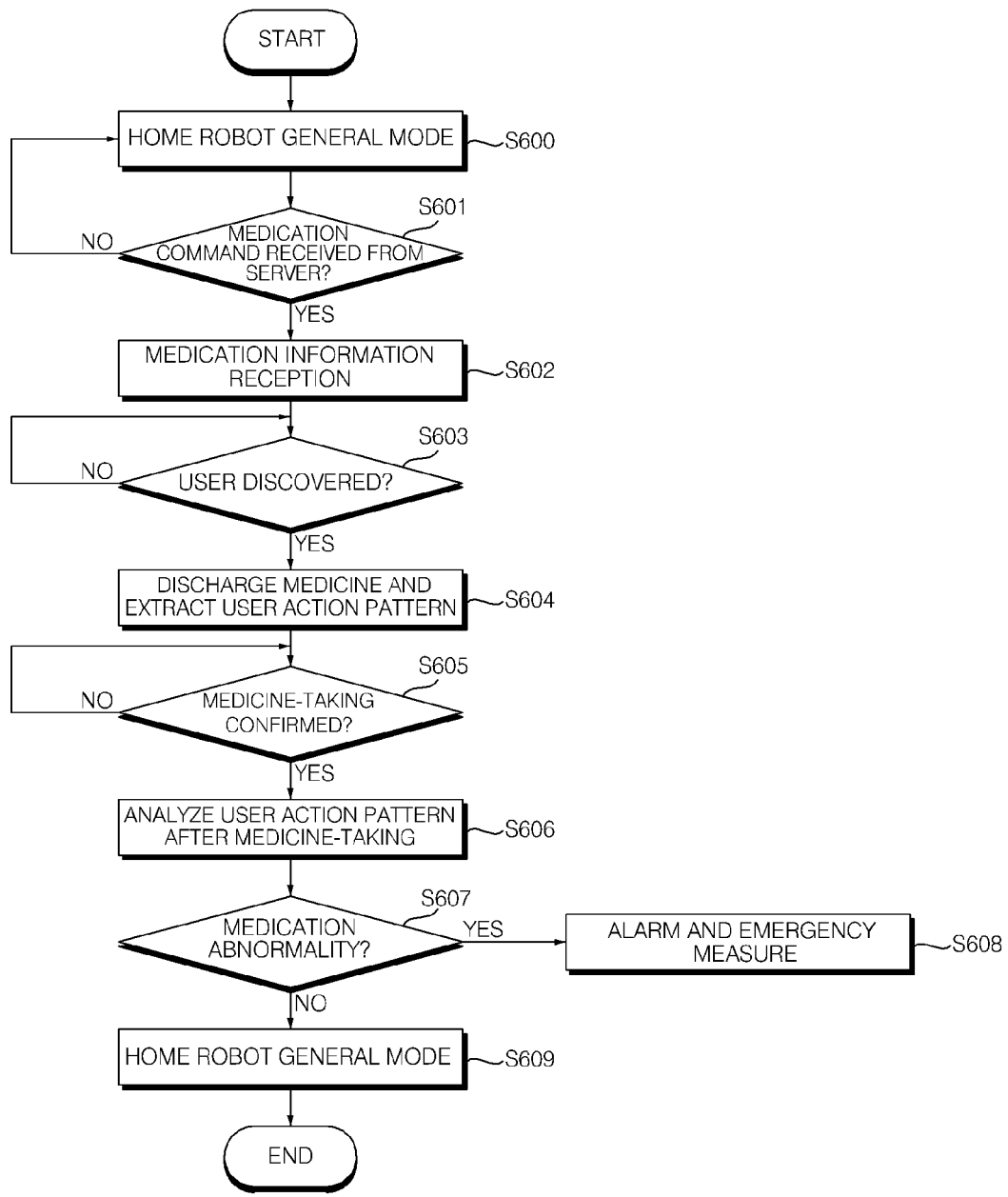
FIG. 11 is a flowchart illustrating a medication service control method of the home robot of FIG. 10.

FIG. 11 is a flowchart illustrating a medication service control method of the home robot 100 of FIG. 10.

First, the home robot 100 functions as a general home robot 100.

That is, in a general mode, the home robot 100 may provide an entertainment function to a user, and, for example, perform music, weather, news and home appliance services and/or a conversation mode (S600).

At this time, upon receiving a medication command from the server 2 according to a medication schedule (S601), the home robot 100 changes the general mode to a healthcare mode.

Namely, the home robot 100 receives a medication command and medication information from the server 2 according to a medication schedule of a specific user (S602). The medication information may include information about a medication target of the current medication schedule, information about the type of a specific medicine to be taken, information about a medication method, etc.

The controller 140 of the home robot 100 scans the face of a discovered user based on the received medication information while the robot travels around, to determine whether the specific user is present around the robot (S603). That is, the controller 140 acquires a surrounding image from the image capture unit 120, grasps a feature point of the exterior appearance of a discovered user when the user is present in image data, compares the feature point of the exterior appearance of the user with the medication target information, and determines based on a result of the comparison whether the discovered user is the medication target.

If the discovered user is determined to be the medication target, the home robot 100 establishes a connection to the server 2 and receives medication information of the medication target from the server 2. At this time, the received medication information may include information about medication execution of the previous cycle, etc. The home robot 100 moves in front of the discovered user, informs the user of an appropriate medication time, and discharges an appropriate medicine. The controller 140 acquires image data extracted through the camera from the image capture unit 120, analyzes the image data, and then extracts an action pattern of the user (S604).

Then, the controller 140 defines the extracted current user action pattern, reads an action pattern in the previous medication execution from the medication information of the user, and determines whether the current action pattern is beyond the previous action pattern.

This action pattern comparison may be performed by comparing images of a medicine-taking action of the user in the current medication cycle with images of the medicine-taking action of the user in the previous medication cycle to determine whether the user has accurately performed medicine-taking in the current cycle (S605).

Upon determining that the user has accurately performed medicine-taking in the current cycle, the controller 140 acquires image data of the user through the camera. The controller 140 may extract an action of the user after medicine-taking through the acquired image data (S606).

At this time, the controller 140 checks whether the user takes an action such as flopping down, falling down or staggering after medicine-taking, analyzes such a pattern through keywords and deep learning, and stores a result of the analysis.

In addition, the controller 140 may measure biometric information of the user through the sensor units 170 and acquire the resulting sense signal. This biometric information sense signal may be an acquired sense signal about a temperature variation, heartbeat or the like of the user.

Then, the sense signals about the action pattern and biometric information of the user may be transmitted to the server 2. Then, the server 2 may store received information in a database for utilization as comparative data in the next cycle, determine the state of the user after medicine-taking based on the received information, and transmit a command based on a result of the determination to the home robot 100.

Next, when the home robot 100 remotely receives the determination result of the user's state or an additional information request from the server 2, it may determine whether additional information of the user can be provided. That is, the home robot 100 may again determine whether the measurement of biometric information sufficient to determine the user's state has been made.

Upon determining that the sufficient biometric information measurement has been made (S607), the home robot 100 determines whether the server 2 remotely determines that the user is abnormal due to medication.

When the home robot 100 receives a command about medication abnormality of the user from the server 2, it generates an alarm and performs operations for an emergency measure, etc. (S608).

Namely, the home robot analyzes image data of the user after medicine-taking, stores a result of the analysis, transmits the stored analysis result to the server 2, measures biometric information of the user, and transfers the resulting information to the server 2. In this case, for example, upon determining through the image data that the user flops down and determining through the biometric information that the user's temperature suddenly rises, the server 2 may determine that the current situation requires an alarm and an emergency measure, and transmit a result of the determination to the home robot.

As a result, the home robot 100 may generate a voice or siren alarm to inform surrounding persons that the user is abnormal. In addition, the home robot 100 may operate an emergency communication network associated with the emergency situation to call a linked hospital, emergency center or the like for help.

Upon determining that there is no medication abnormality in the user, the home robot 100 ends the healthcare mode and again returns to the general mode (S609).

The constructions and methods of the embodiments as described above are not limitedly applied to the robot system according to the present invention; rather, all or some of the embodiments may be selectively combined to achieve various modifications.

Meanwhile, the control methods of the robot 1 system according to the embodiments of the present invention may be implemented as code that can be written on a processor-readable recording medium and thus read by a processor. The processor-readable recording medium may be any type of recording device in which data is stored in a processor-readable manner. The processor-readable recording medium may include, for example, a ROM, a RAM, a CD-ROM, a magnetic tape, a floppy disk, and an optical data storage device, and may be implemented in the form of a carrier wave transmitted over the Internet. In addition, the processor-readable recording medium may be distributed over computer systems connected via a network such that processor-readable code is written thereto and executed therefrom in a decentralized manner.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

| [Description of Reference Numerals] | | | |
|---|---|---|---|
| 1: | AI robot | 2: | server |
| 170: | sensor unit | 120: | image capture unit |
| 160: | driving unit | 140: | controller |
| 190: | communication unit | 100: | home robot |

The invention claimed is:

1. A method of controlling an artificial intelligence (AI) robot, the method comprising:
    matching, by the AI robot, a user with a medication target according to a medication schedule;
    discharging a medicine set for the user;
    acquiring first image data including a medicine-taking action of the user after the discharging of the medicine;
    comparing the first image data with previous image data including a previous medicine-taking action of the user from a previous cycle through deep learning to generate a first determination result indicating whether the user has taken the medicine correctly;
    acquiring second image data of the user after the medicine-taking;
    acquiring a sense signal including biometric data of the user after the medicine-taking;
    generating a second determination result indicating whether there is an abnormality in the user based on the second image data and the sense signal including the biometric data; and
    in response to the second determination result indicating that there is the abnormality in the user, performing an emergency measure.

2. The method according to claim 1, wherein the AI robot comprises a body comprising a medicine container formed inside thereof, the medicine container having a space defined to contain the medicine, and an inlet/outlet port formed on an outer surface thereof, the inlet/outlet port injecting or discharging the medicine therethrough.

3. The method according to claim 2, comprising:
    analyzing an action pattern of the user based on the first image data through the deep learning; and
    combining the sense signal and the action pattern of the user to determine whether there is the abnormality in the user.

4. The method according to claim 3, wherein the biometric data comprises information about a heart rate of the user and a temperature of the user.

5. The method according to claim 4, wherein the matching the user with the medication target comprises:
   searching for the user while the AI robot moves; and
   matching image data of the searched user with information about the medication target upon acquiring the image data of the searched user.

6. The method according to claim 5, further comprising estimating a location where the user is located and moving to the estimated location.

7. The method according to claim 6, wherein the AI robot receives medication command information from a server according to the medication schedule.

8. The method according to claim 6, wherein the AI robot receives information about the medication schedule directly from the user and searches for the medication target according to the medication schedule stored therein.

9. The method according to claim 4, wherein the matching a user with a medication target comprises calling a surrounding user through notification thereto according to the medication schedule and reading image data of the surrounding user to determine whether the surrounding user is the medication target.

10. An artificial intelligence (AI) robot comprising:
    a body for defining an exterior appearance of the AI robot and configured to contain a medicine to be discharged according to a medication schedule;
    a support for supporting the body;
    an image sensor configured to capture an image within a traveling zone of the AI robot; and
    a controller configured to:
      discharge the medicine to a user according to the medication schedule,
      acquire first image data including a medicine-taking action of the user after the discharging of the medicine,
      compare the first image data with previous image data including a previous medicine-taking action of the user from a previous cycle through deep learning to generate a first determination result indicating whether the user has taken the medicine,
      acquire second image data of the user after the medicine-taking,
      acquire biometric data of the user after the medicine-taking, and
      generate a second determination result indicating whether there is an abnormality in the user based on the second image data and the biometric data.

11. The AI robot according to claim 10, wherein the controller is further configured to:
    in response to the second determination result indicating that there is the abnormality in the user, perform an emergency measure.

12. The AI robot according to claim 10, further comprising an inlet/outlet port formed on an outer surface of the body to inject or discharge the medicine therethrough.

13. The AI robot according to claim 10, wherein the controller is further configured to:
    analyze an action pattern of the user based on the first image data through the deep learning, and
    combine the biometric data and the action pattern of the user to determine whether there is the abnormality in the user.

14. The AI robot according to claim 13, wherein the biometric data comprises information about a heart rate of the user and a temperature of the user.

15. The AI robot according to claim 10, wherein the support comprises a traveling part for moving the AI robot,
    wherein the controller drives the traveling part such that the AI robot searches for the user while moving.

16. The AI robot according to claim 15, wherein the controller is further configured to estimate a location where the user is located and drive the traveling part to move the AI robot to the estimated location.

17. The AI robot according to claim 16, wherein the AI robot receives medication command information from a server according to the medication schedule.

18. The AI robot according to claim 16, further comprising an interface configured to receive information about the medication schedule directly from the user,
    wherein the storage part is configured to search for a medication target according to the medication schedule stored therein.

19. The AI robot according to claim 10, wherein the AI robot is configured to call a surrounding user through notification thereto according to the medication schedule and read image data of the surrounding user to determine whether the surrounding user is a medication target.

* * * * *